US011000652B2

(12) United States Patent
Lastow

(10) Patent No.: US 11,000,652 B2
(45) Date of Patent: May 11, 2021

(54) DRY POWDER INHALER

(71) Applicant: Iconovo AB, Lund (SE)

(72) Inventor: Orest Lastow, Torna Haellestad (SE)

(73) Assignee: ICONOVO AB

( * ) Notice: Subject to any disclaimer, the term of this patent is extended or adjusted under 35 U.S.C. 154(b) by 530 days.

(21) Appl. No.: 15/572,495

(22) PCT Filed: May 9, 2016

(86) PCT No.: PCT/EP2016/060275
§ 371 (c)(1),
(2) Date: Nov. 7, 2017

(87) PCT Pub. No.: WO2016/180753
PCT Pub. Date: Nov. 17, 2016

(65) Prior Publication Data
US 2018/0140785 A1 May 24, 2018

(30) Foreign Application Priority Data

May 8, 2015 (SE) .................................... 1550594-4
May 8, 2015 (SE) .................................... 1550595-1

(51) Int. Cl.
*A61M 15/00* (2006.01)
*A61M 11/00* (2006.01)

(52) U.S. Cl.
CPC .... *A61M 15/0003* (2014.02); *A61M 15/0065* (2013.01); *A61M 11/002* (2014.02); *A61M 2202/064* (2013.01); *A61M 2206/14* (2013.01)

(58) Field of Classification Search
CPC .. A61M 15/003–0008; A61M 15/0048; A61M 15/0065; A61M 11/02
See application file for complete search history.

(56) References Cited

U.S. PATENT DOCUMENTS 5,243,970 A * 9/1993 Ambrosio ......... A61M 15/0065
128/203.12
5,351,683 A   10/1994 Chiesi et al.
(Continued)

FOREIGN PATENT DOCUMENTS

DE     19518810 A1   11/1996
EP     0069715       1/1983
(Continued)

*Primary Examiner* — Valerie L Woodward
(74) *Attorney, Agent, or Firm* — Fishman Stewart PLLC

(57) ABSTRACT

A dry powder inhaler may include at least one air inlet, at least one air outlet, an air channel between said air inlet and outlet, and at least one medicament reservoir. The inhaler may include a dosage mechanism for arranging at least one dose of a medicament from said medicament reservoir between the air channel and the air outlet such that said at least one dose may be delivered upon inhalation at said air outlet. The dosage mechanism may include a dose disc with at least one cavity, wherein the dose disc may be rotatable between a dose collecting position, in which the cavity may be positioned in the medicament reservoir, and a dose administering position, in which the cavity may lie underneath the air channel. The inhaler may also include a floor disc abutting the dose disc underneath the cavity to form a bottom of the cavity for radial emptying of the medicament from the cavity during inhalation. Alternatively, the inhaler may include a floor disc abutting the dose disc underneath the cavity to form a bottom of the cavity and support the medicament in the cavity, wherein said dose disc may rotate in relation to the floor disc when the dose disc is rotated between the dose collecting position and the dose administering position to grind any residual medicament in the cavity.

21 Claims, 4 Drawing Sheets

(56) References Cited

U.S. PATENT DOCUMENTS

| | | | |
|---|---|---|---|
| 5,505,196 A | | 4/1996 | Herold et al. |
| 5,702,362 A | * | 12/1997 | Herold ............... A61M 31/00 |
| | | | 604/58 |
| 6,119,688 A | * | 9/2000 | Whaley ............ A61M 15/0065 |
| | | | 128/203.12 |
| 6,240,918 B1 | | 6/2001 | Ambrosio et al. |
| 6,484,718 B1 | | 11/2002 | Schaeffer et al. |
| 6,810,874 B1 | * | 11/2004 | Koskela ................ A61P 29/00 |
| | | | 128/203.15 |
| 6,978,780 B1 | | 12/2005 | Marnfeldt et al. |
| 2002/0148469 A1 | * | 10/2002 | O'Leary ........... A61M 15/0065 |
| | | | 128/203.15 |
| 2007/0272763 A1 | * | 11/2007 | Dunne ................... A61M 11/02 |
| | | | 239/8 |
| 2013/0000639 A1 | | 1/2013 | Galluppi et al. |

FOREIGN PATENT DOCUMENTS

| | | | |
|---|---|---|---|
| EP | 0237507 | A1 | 9/1987 |
| EP | 2058025 | A1 | 5/2009 |
| GB | 2041763 | | 9/1980 |
| RU | 2002467 | C1 * | 11/1993 |
| WO | WO-93/00123 | A1 | 1/1993 |
| WO | WO-2005/016422 | A1 | 2/2005 |
| WO | WO-2009/145673 | A2 | 12/2009 |

\* cited by examiner

Fig. 4
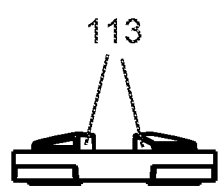
Fig. 5C
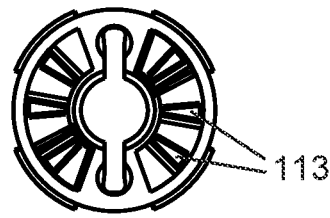
Fig. 5D      Fig. 5A      Fig. 5E
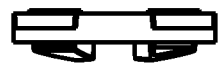
Fig. 5F
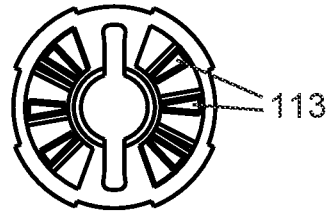
Fig. 5B

DRY POWDER INHALER

CROSS-REFERENCE TO RELATED APPLICATIONS

This application claims priority to International Patent Application No. PCT/EP2016/060275, filed on May 9, 2016, Swedish Patent Application No. 1550594-4, filed on May 8, 2015, and Swedish Patent Application No. 1550595-1, filed on May 8, 2015, the contents of all of which are incorporated herein by reference in their entireties.

TECHNICAL FIELD

This invention pertains in general to the field of medicament inhalers, and more particularly to dry powder inhalers. Even more particularly, the invention pertains to a medicament inhaler comprising a dosage mechanism and a floor disc abutting the dosage mechanism.

BACKGROUND

Inhalers have been widely used in the pharmaceutical field for treatment of respiratory and/or other diseases. Numerous drugs, medications and other substances are inhaled into the lungs using the inhalers for rapid absorption of the drug etc. in the blood stream and for local action in the lung.

Inhaled drugs fall into two main categories, one being in the form of liquids, including suspensions, and the other being powders. The choice of liquids or powders depends on the characteristics of the drugs, medications, etc. to be inhaled.

The most common type of inhaler is the pressurized metered-dose inhaler. In this type of inhaler medication is most commonly stored in solution in a pressurized canister that contains a propellant, although it may also be a suspension. The canister is attached to a plastic, hand-operated actuator. On activation, the metered-dose inhaler releases a fixed dose of medication in aerosol form.

Another kind of inhaler is a nebulizer, which supplies medication as an aerosol created from an aqueous formulation.

The kind referred to herein is yet another type, in the form of a dry powder inhaler. A dry powder inhaler releases a pre-metered, capsuled, dose or a device-metered dose of powdered medication that is inhaled through the inhaler. Inhalers with a device-metered dose of powdered medication are normally inhalers with a medication reservoir containing powdered medication, from which metered doses are withdrawn through the use of different dose metering arrangements, said doses then being inhaled.

Dry powder inhalers need to deliver a particle size that is predominantly below 5 microns, and preferably between 1 micron and 3.3 microns, for maximum effectiveness. However, such small particles are often very cohesive due to high surface energy. Agglomeration may be worsened by moisture and/or when the medication comprises more than one active substance, since the different active substances may have such properties as to form agglomerations with each other or with pharmaceutical carriers etc. Agglomeration of small particles is a problem which results in the active particles leaving the inhaler as large agglomerates.

EP0237507 discloses a powder inhaler with a device metered dose, comprising a medicament chamber, a dosing mechanism, and a flow path from an air inlet to an air/medicament outlet. Deflectors are arranged in the flow path to increase deaggregation of medicament. However, this device is limited to medicaments having one active substance or active substances that are compatible with each other during storage. Additionally, medicament will accumulate at the deflectors thus decreasing uniformity of the dosage.

An additional problem of prior art inhalers is that they are either suitable for micronized formulations or carrier based formulations never both or combinations of these.

In view of these drawbacks and limitations of the prior art, what is needed is a dry powder inhaler device in which effective and satisfactory dispersion of the dry powder is obtained, which inhaler can administer medicament comprising substances which are incompatible in a mixture, and an inhaler with increased deaggregation and a more uniform dosage, in which inhaler there is no risk of multiple dosing, as well as an inhaler which is robust and suitable for both micronized formulations and/or carrier based formulations.

SUMMARY

Accordingly, the present invention preferably seeks to mitigate, alleviate or eliminate one or more of the above-identified deficiencies in the art and disadvantages singly or in any combination and solves at least the above mentioned problems by providing in a first aspect a dry powder inhaler comprising: at least one air inlet, at least one air outlet, and an air channel between said at least one air inlet and said at least one air outlet; at least one medicament reservoir; a dosage mechanism for arranging at least one dose of a medicament from said at least one medicament reservoir between the air channel and the air outlet such that said at least one dose may be delivered upon inhalation at said air outlet, wherein the dosage mechanism comprises a dose disc with at least one cavity, wherein the dose disc may be rotated between a dose collecting position wherein the cavity is positioned in the medicament reservoir, and a dose administering position wherein the cavity lies underneath the air channel; and a floor disc abutting the dose disc underneath the cavity to form a bottom of the cavity for radial emptying of the medicament from the cavity during inhalation.

In a second aspect there is provided a dry powder inhaler comprising: at least one air inlet, at least one air outlet, and an air channel between said at least one air inlet and said at least one air outlet; at least one medicament reservoir; a dosage mechanism for arranging at least one dose of a medicament from said at least one medicament reservoir between the air channel and the air outlet such that said at least one dose may be delivered upon inhalation at said air outlet, wherein the dosage mechanism comprises a dose disc with at least one cavity, wherein the dose disc may be rotated between a dose collecting position wherein the cavity is positioned in the medicament reservoir, and a dose administering position wherein the cavity lies underneath the air channel; and a floor disc abutting the dose disc underneath the cavity to form a bottom of the cavity and support the medicament in the cavity, wherein said dose disc rotates in relation to the floor disc when the dose disc is rotated between the dose collecting position and the dose administering position to grind any residual medicament in the cavity.

Further advantageous embodiments are disclosed below and in the appended patent claims.

BRIEF DESCRIPTION OF THE DRAWINGS

These and other aspects, features and advantages of which the invention is capable will be apparent and elucidated from the following description of embodiments of the present invention, reference being made to the accompanying drawings, in which;

FIG. 4 is a perspective view showing a medicament scraper for use in the inhaler in FIG. 1.

FIGS. 5A-5F shows top, bottom and four side views of the medicament scraper in FIG. 4.

DETAILED DESCRIPTION

The following description focuses on an embodiment of the present invention applicable to a medicament inhaler, and in particular to a dry powder drug inhaler with more than one medicament reservoir, such as two medicament reservoirs. However, it will be appreciated that the invention is not limited to this application but may be applied to many other inhalers having an inlet and an outlet, as well as a medicament reservoir.

Figures 1, 2:
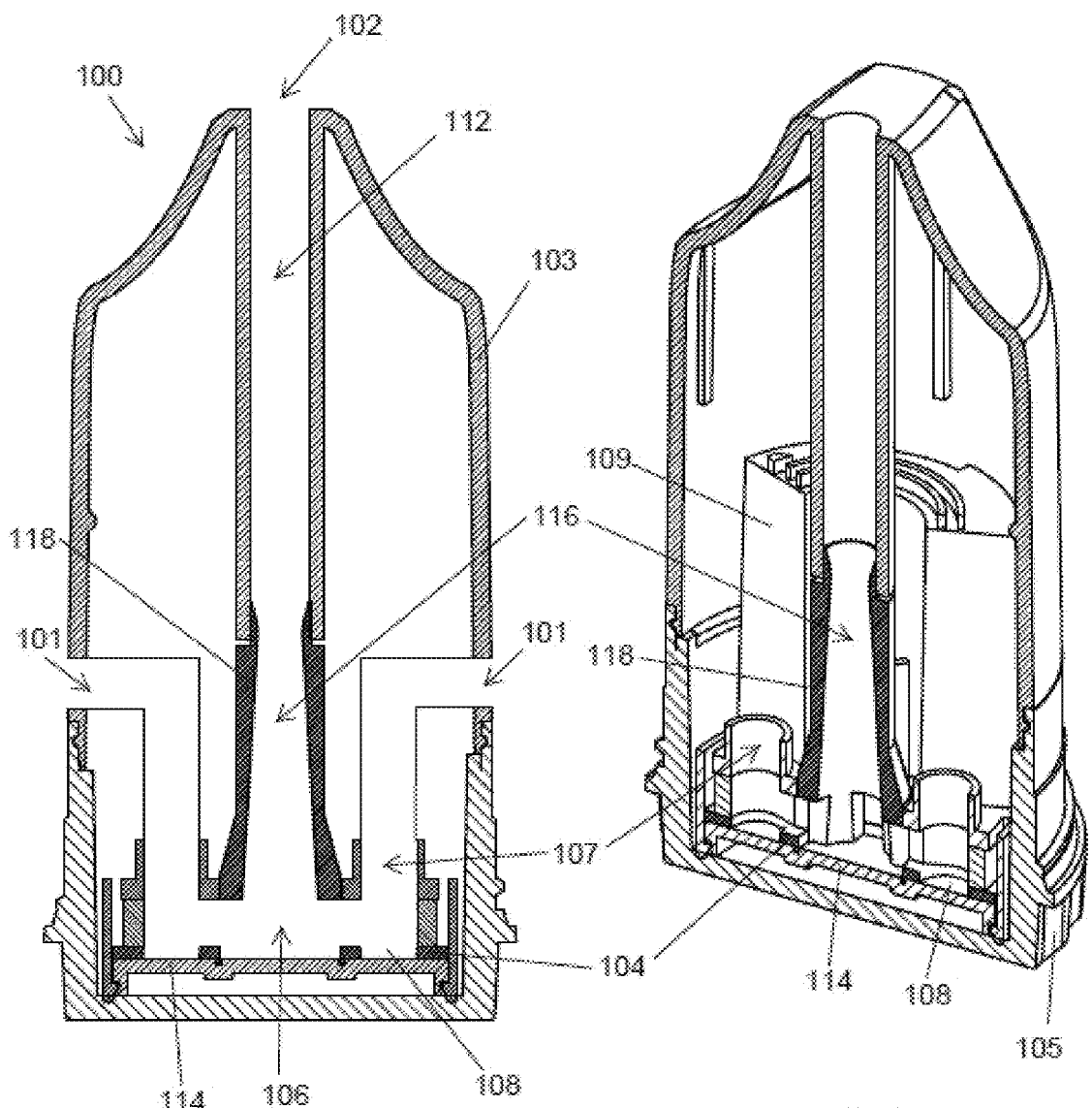
FIG. 1 is a cross sectional view along a longitudinal axis of an inhaler in the dose administering position according to one embodiment of the present invention.
FIG. 2 is a perspective and cross sectional view of the inhaler in FIG. 1. Air inlets are omitted from FIG. 2 for clarity.

FIGS. 1 and 2 illustrate a dry powder drug inhaler 100. The dry powder drug inhaler 100 comprises air inlets 101 and an air outlet 102. The outlet 102 is arranged at a first end of the dry powder drug inhaler 100 while the inlets 101 are arranged at a zone in an opposite second end of the dry powder drug inhaler 100. The outlet 102 is arranged centrally along the longitudinal axis of the dry powder drug inhaler 100. The inlets 101 may be arranged at the periphery of the dry powder inhaler 100 in a radial position in relation to the longitudinal axis of the dry powder drug inhaler 100, such that the inlets 101 lead inhaled air transversally and radially towards the central portion of the dry powder inhaler 100.

Although not illustrated in FIGS. 1 and 2, the inlets 101 may also be positioned with a direction that is parallel to the central axis of the dry powder inhaler 100.

The number of inlets and outlets may be different from what is disclosed in FIGS. 1 and 2. The number of inlets may for example be adjusted in accordance with needs and specific inhaler design such that a number of smaller air inlets, for reducing pressure fall over the inhaler, are arranged circumferentially on the dry powder inhaler 100. In a similar manner the number of air outlets may be adjusted in accordance with needs and specific inhaler design.

The different parts of the dry powder inhaler 100 may be manufactured in a suitable material, such as injection moldable plastics, such as thermoplastics.

The dry powder inhaler 100 comprises three major parts in the form of (i) an upper proximal reservoir housing 103 with an inhalation chimney 112, (ii) a dosage mechanism 118 comprising a dose disc 104 having at least one cavity 108, a mixing and deaggregation chamber 106 adjacent to the at least one cavity 108, and a conduit 116 extending distally from the chamber 106, and (iii) a lower distal twister 105 having a floor disc 114. The reservoir housing 103 and the twister 105 cooperate so as to house the dosage mechanism 118 and the floor disc 114 in between housing 103 and twister 105. The chimney 112 of the reservoir housing 103 cooperates with the conduit 116 of the dosage mechanism 118 such that the dose disc 104 may be rotated between a dose administering position and a dose collecting position when the reservoir housing 103 is rotated. The floor disc 114 is connected to twister 105 so that floor disc 114 only moves when twister 105 is rotated as will be described further below. This may be accomplished by connecting the floor disc 114 and the twister 105 via interconnecting grooves and ribs, or letting the twister 105 extend longitudinally around the floor disc 114 as disclosed for example in FIG. 1. Preferably, the rotation of the dose disc 104 has two end positions corresponding to the dose administering position and the dose collecting position in its relation with the reservoir housing 103 in a known manner.

Figure 3:
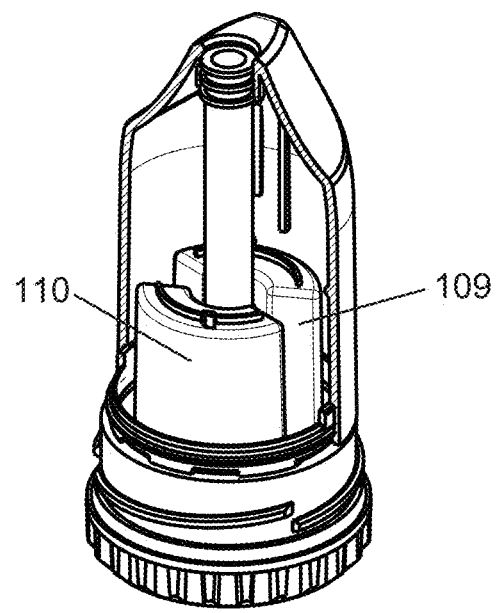
FIG. 3 is a perspective and partial cross sectional view of the inhaler in FIG. 1 showing two medicament reservoirs. Air inlets are omitted from FIG. 3 for clarity.
Figure 6:
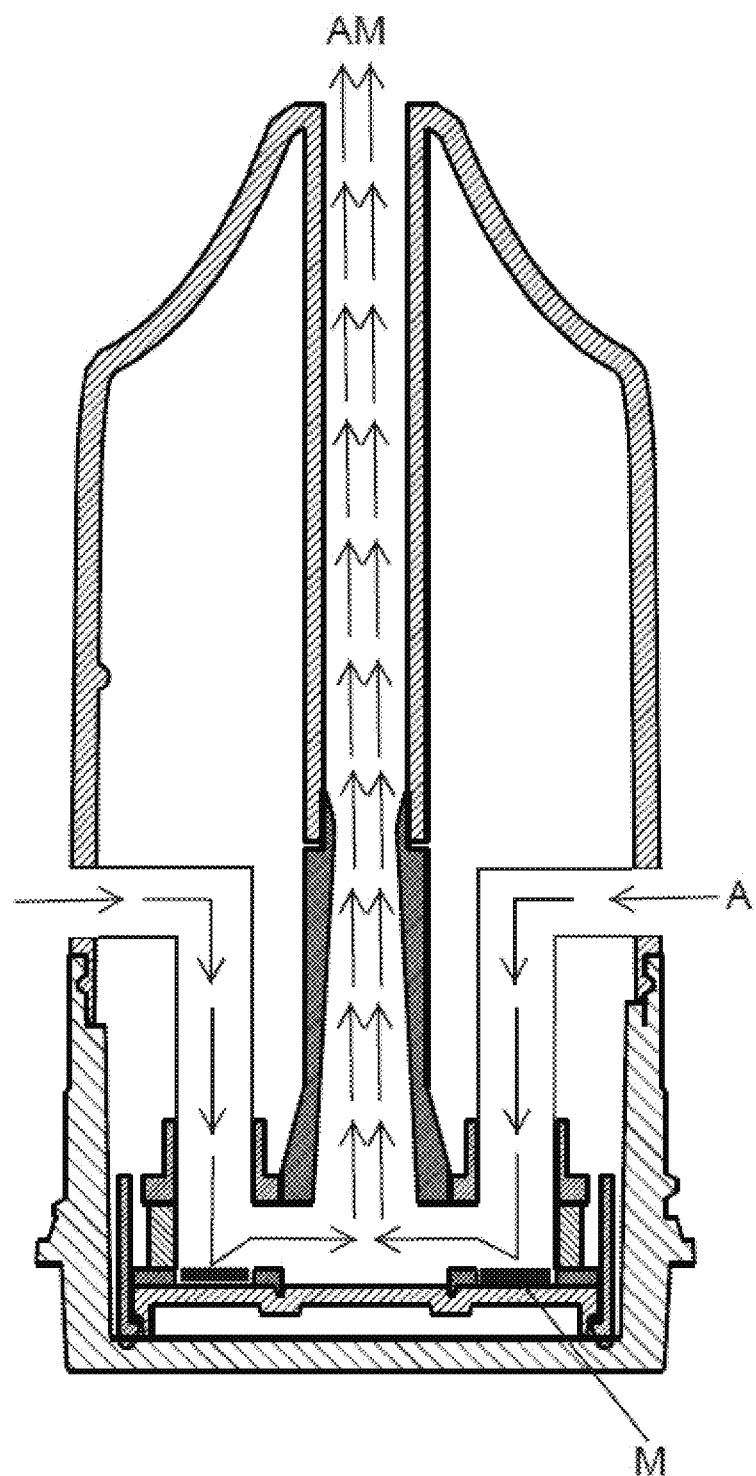
FIG. 6 is a cross sectional view along a longitudinal axis of the inhaler in FIG. 1 wherein the air (A) and air/medicament flows (AM) through this inhaler are disclosed.

The dose administering position is illustrated in FIGS. 1 and 2. In the dose administering position, the inlets 101 are in communication with the mixing and deaggregation chamber 106 via air channels 107. The air channels 107 direct the flow of air from inlets 101 initially downwards onto cavities 108 in the dose disc 104. Hence, in the dose administering position the cavities 108 lie underneath and in line with the air channels 107. The combination of the inhaled air from channels 107 and the medicament from cavities 108 then flows radially to the chamber 106 as will be described further below with respect to FIG. 6. When the dose disc 104 is rotated into a dose collecting position (not shown), the chamber 106 and the cavities 108 are rotated away from communication with the inlets 101 and air channels 107. Instead, the cavities 108 are rotated into medicament reservoir 109 (shown in FIG. 2 and FIG. 3) and medicament reservoir 110 (shown in FIG. 3), wherein the cavities 108 may collect a medicament housed in the reservoirs 109 and 110. The medicament contained in the medicament reservoir 109 may be a medicament different from the medicament contained in the medicament reservoir 110. Due to the presence of two reservoirs 109 and 110, the inhaler 100 may deliver two substances in one inhalation, said two substances otherwise being incompatible meaning that these two substances would not be possible to be comprised in one joint reservoir. Thus, the dry powder inhaler device 100 can effectively and satisfactorily disperse two dry powders and can administer a medicament comprising two or more substances which are incompatible in a mixture or are preferably stored in separate reservoirs for other reasons.

It is possible to arrange the dose disc 104 and the cavities 108 thereof such that when a first set of two cavities 108 lie underneath and in line with the air channels 107, i.e. in a dose administering position, a second set of two cavities 108 are positioned in the medicament reservoirs 109, 110 respectively. In this arrangement the inhaler has two medicament reservoirs, two air inlets, and one dose disc with four cavities. Additionally, the distribution of the cavities 108 on the dose disc 104 is such that the dose disc 104 may be rotated in one direction only meaning that when the second set of two cavities 108 lie underneath and in line with the air channels 107, the first set of cavities 108 are positioned in the medicament reservoirs 109, 110 respectively. It is also possible for the dose disc 104 to be rotated in a first direction so that cavities 108 lie underneath and in line with the air channels 107 in a dose administering position, and then for the dose disc 104 to be rotated in the opposite direction into the dose collecting position, and thereafter again for the dose disc to be rotated in said first direction back into the dose administering position. When the dose disc 104 is rotated in a first direction into the dose administering position and the opposite direction into the dose collecting position, the dose disc 104 may have rotational stops in the dose administering position and the dose collecting position, respectively, to ensure accurate alignment of the cavities 108 under air channels 107 and positioning in the medicament reservoirs 109, 110 respectively.

It is also envisioned that an inhaler provided with more than two, such as three, four, five, or six, reservoirs 109, 110 with the same arrangement of inlets, outlets, air channels, dose disc, cavities etc., is within the ambit of the present invention. For example, the inhaler 100 may have three medicament reservoirs 109, three air inlets 101, and a dose disc with three cavities 108. Alternatively, the inhaler 100 may have four medicament reservoirs 109, four air inlets 101, and a dose disc with four cavities 108. It is preferred however that the inhaler 100 have two air inlets 101, two air channels 107, one air outlet 102, two medicament reservoirs 109, 110, and one dose disc 104 with two cavities 108.

It is also envisioned that the inhaler 100 may be provided with a different dosage mechanism than the one disclosed above, for example electrical drive of different parts, and using paddles instead of the dose disc 104. However, use of the dosage mechanism 118 having the dose disc 104 and its cooperation with chimney 112 of the upper housing 103 and the reservoirs 109, 110 allows for a very cost effective solution while simultaneously ensuring high dose accuracy and the other benefits disclosed herein.

The floor disc 114 is located underneath dose disc 104 and extends substantially across the diameter of the dose disc 104. The floor disc 114 abuts the dose disc 104 and closes the bottom of the cavities 108 to provide support for the medicament in cavities 108 after collection of the medicament from the reservoirs 109 and 110. Thus, the floor disc 114 forms a bottom of the cavity 108, wherein said dose disc 104 rotates in relation to the floor disc 114 when the dose disc 104 is rotated between the dose collecting position and the dose administering position. Floor disc 114 moves with lower twister 105 when the twister 105 is rotated. The floor disc 114 does not rotate independently of lower twister 105. In use the dose disc 104 is rotated independently of the floor disc 114 while remaining in contact with floor disc 114. The arrangement of the dose disc 104 to the floor disc 114 allows the inhaler to be used with free flowing powder medicaments such as carrier based formulations that are not particularly susceptible to aggregation in the cavities 108. The floor disc 114 supports the free flowing powder so that cohesive forces between particles of the powder are not necessary to retain the powder in the cavity. The arrangement further allows for a more robust inhaler that can absorb shock, shaking or other types of impact with little to no disturbance or loss of medicament from cavities 108 prior to inhalation. Even if the inhaler is vigorously shaken resulting in displacement of some medicament from a cavity 108, there is no risk of multiple dosing as the dose disc 104 is not rotated into the medicament reservoirs (again) prior to inhalation of the medicament during correct use of the inhaler. The arrangement also allows for removal of any medicament residue from the cavity 108 when the dose disc 104 is rotated over the floor disc 114. Frictional forces between the dose disc 104 and the floor disc 114 during the rotational movement result in attrition or grinding of the medicament residue that is later inhaled by the user or returned to the medicament reservoirs. These frictional forces are maximized during simultaneous rotation of the dose disc 104 and the floor disc 114 against each other by rotating the reservoir housing 103 and the twister 105 in opposite directions. This prevents accumulation of medicament residue in the cavities 108 and is most beneficial when using the inhaler with a medicament(s) susceptible to aggregation in the cavities 108. As illustrated in FIGS. 1 and 2, the floor disc 114 may be suspended by a small distance above lower distal twister 105 although it is possible that the floor disc 114 may lie directly on top of lower distal twister 105.

The air channels 107 have a right angle conformation as disclosed in the embodiment in FIG. 1. The right angle conformation is such that the air channels 107 start at inlets 101 and extend downstream (during inhalation) in a central and transversal direction, where after they bend downwards at a right angle (90 degrees) to extend in a longitudinal and distal direction before ending above and in line with the cavities 108 (in the dose administering position). In this way, when medicament lies in the cavities 108, the air flow direction will facilitate initial deaggregation of the medicament from the cavities 108. This ensures that the medicament in the cavities 108 will be dispersed into the air flow and enter into the chamber 106. This arrangement means for example that the reservoirs 109, 110 may comprise a dry powder medicament in the form of a micronized formulation or a carrier based formulation, or mixtures thereof. The inhaler 100 may then for example comprise a dry powder medicament in form of a micronized formulation in the first reservoir 109 and a free-flowing dry powder medicament in form of a carrier based formulation in the second reservoir 110.

It is of course not necessary for the air channels 107 to have a right angle conformation as illustrated in FIG. 1. The air channels 107 could also curve inwards and downwards from inlets 101 before ending above and in line with the cavities 108. Other air channel conformations are considered within the ambit of the invention provided the inhaled air flow facilitates deaggregation of the medicament from the cavities.

Depending on the medicament to be administered, and the formulation thereof, the cavities 108 may take the form of a single circular shape when viewed from directly above or below the inhaler 100 as illustrated by the semi-circular shape of cavities 108 in FIG. 2. The single circular shape will be of approximately the same size and shape as the air channel 107. This will be most suitable when the medicament is not readily susceptible to aggregation and/or a large dose is desired. Other medicaments which tend to aggregate more may form an undesirable "plug" in the cavity 108 which is not readily dispersible during inhalation. Then it may be preferable to make several cavities 108 each having a relatively smaller diameter than a single circular shape as illustrated in FIGS. 1 and 2. The several smaller cavities will continue to lie underneath one of the air channels 107 which remains unchanged in size and shape. An inhaler with several smaller cavities lying underneath one air channel 107 also allows for delivery of a smaller amount of powder. This feature also adds the possibility to combine or adapt the inhaler 100 for deliverance of micronized formulations and/or carrier based formulations.

The reservoirs 109, 110 may be provided with medicament scrapers 113 illustrated in FIGS. 4 and 5A-5F. The scrapers are suspended at the bottom of the reservoirs 109, 110 such that they bear upon the dose disc 104. The scrapers will pass over the cavities 108 of the dose disc 104 so that excessive medicament is removed from the cavities 108 to ensure correct dose volume. The scrapers will also aid in compacting medicament in the cavities 108 which will improve retention of medicament in cavities 108 when the dose disc has been rotated into the dose administering position. Since the scrapers 113 are suspended at the bottom of the reservoirs 109, 110 they will automatically slide along the upper proximal surface of the dose disc 104, when the dose disc 104 is rotated between the dose administering position and dose collecting position. Preferably, each reservoir 109, 110 has a number of scrapers evenly distributed along the bottom of the reservoirs 109, 110. In this way the scrapers do not only aid in obtaining correct dose volume and dose compacting but also aid in distributing medicament at the bottom of the reservoirs 109, 110. The number of scrapers per reservoir 109, 110 could for example be selected in the interval of 1 to 6, such as 2 to 4, such as 3. It is also envisioned that the scrapers are arranged in an uneven distribution in the reservoirs 109, 110 if certain reservoirs are configured such that an uneven distribution of the scrapers will have a beneficial effect on the medicament distribution along the bottom of the reservoirs 109, 110

During inhalation the medicament is emptied radially from the cavity with the air flow from the air channels 107 into the chamber 106 wherein the air/medicament streams from the different air channels 107 and cavities 108 will cross, such that the medicament agglomerates will collide to increase deaggregation, where after a jet stream of finely dispersed medicament and air will continue through conduit 116 and inhalation chimney 112 out of the inhalator 100 through outlet 102 and into the lungs of the user. This radial emptying of the cavities 108 will be described further below with respect to FIG. 6. The conduit 116 and the chimney 112 increases jet formation, allowing for a maintained low aggregation of medicament, hence increasing potential of medicament to reach far into the lungs of the patient. The conduit and chimney are generally tubular, but could optionally be provided with deflectors, to further increase jet creation. Such deflectors could be bumps or spiral-shaped ridges, extending along the length of the conduit and/or chimney from the chamber 106 to the air outlet 102. The chimney 112 does not necessarily have to be directed upwardly; it can just as well be directed downwardly or to the sides, whereby the outlet 102 is instead positioned at the bottom or on the sides, respectively. Additionally, the chimney 112 does not have to be generally tubular, but could be bent or sinus-shaped, depending on where on the inhaler 100 it is preferred to position the outlet 102. For flow characteristics and dose reliability and maintenance, it is however preferred to have it directed upwardly and generally tubular with optional deflectors. The general shapes of the conduit 116 and the chimney 112 may also be such as to have differences in cross-sectional area, such as is present in a cone-shaped chimney. In this way, the flow velocity in the conduit and chimney may be regulated so as to help in deaggregation at chosen parts.

During use of the inhaler 100 the user will then simply rotate the upper housing 103 in one direction and thus the dose disc 104 into a dose collecting position if the dose disc is in a dose administering position. Thereafter, the upper housing 103 and the dose disc 104 are rotated preferably into the opposite direction to reach the dose administering position. If the dose disc 104 is already in the dose collecting position then of course the first rotation into the dose collecting position may be omitted. During these rotations, the scraper 113 will fill the cavities 108 of the dose disc 104 in the reservoirs 109, 110. After the dose disc 104 has been rotated into the dose administering position the cavities 108 are filled with medicament—optionally two different medicaments—and lie underneath the air channels 107. Then the user puts his/her mouth at outlet 102 and inhales. During inhalation air A will enter the inhaler 100 through inlets 101 and flow through air channels 107 to disperse and carry therewith the medicament(s) M from the cavities 108 in a radial direction in accordance with the arrows shown in FIG. 6. The air/medicament flow AM will then enter the chamber 106. In the chamber 106, the air/medicament flows AM from the air channels 107 and cavities 108 will cross each other or coincide with each other, such that deaggregation of the medicaments M will increase which may increase dose uniformity since the need for deflectors then is decreased. The flow characteristics, such as jet stream formation, will also increase. This feature allows the possibility to combine or adapt the inhaler 100 for deliverance of micronized formulations and/or carrier based formulations. Of course, it is also possible to combine the feature of crossing or coinciding flows from the two air channels 107 with deflectors, even though the need thereof is decreased. Thereafter, the air/medicament flow AM now comprising air/medicament flows from both air channels 107 and cavities 108, will go up through the conduit 116, the inhaler chimney 112, and finally through outlet 102 into the lungs of the user. A similar sequence of steps is then repeated the next time the inhaler 100 is required i.e. the user rotates the upper housing 103 and thus the dose disc 104 into a dose collecting position to fill the cavities 108 with a medicament(s) then the user rotates the dose disc 104 back into the dose administering position and inhales at outlet 102 as described immediately above.

The structure of, and functional relationship between, the cavities 108, reservoirs 109, 110 and the separate dose collecting and dose administering positions allows for no risk of multiple dosing by the user. In use the medicaments remain in the cavities 108 until inhalation. If inhalation is not commenced or is no longer required by the user, the cavities 108 carrying the medicaments may be rotated back into the reservoirs 109,110.

Although, the present invention has been described above with reference to specific embodiments, it is not intended to be limited to the specific form set forth herein. Rather, the invention is limited only by the accompanying claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A dry powder inhaler comprising:

at least two air inlets, at least one air outlet, and at least two air channels each between a corresponding one of said at least two air inlets and said at least one air outlet;

at least one medicament reservoir;

a dosage mechanism for arranging at least one dose of a medicament from said at least one medicament reservoir between the air channel and the air outlet such that said at least one dose may be delivered upon inhalation at said air outlet, wherein the dosage mechanism includes a dose disc with at least one cavity, and wherein the dose disc is rotatable between a dose collecting position, in which the cavity is positioned in the medicament reservoir, and a dose administering position, in which the cavity lies underneath one of the air channels, and wherein the dosage mechanism includes a mixing and deaggregation chamber between the at least two air channels, and a conduit extending distally from the mixing and deaggregation chamber towards the at least one air outlet;

a floor disc abutting the dose disc underneath the cavity to form a bottom of the cavity for radial emptying of the medicament from the cavity during inhalation; and an upper proximal reservoir housing with an inhalation chimney interconnecting the conduit and the air outlet, the inhalation chimney cooperating with the conduit to rotate the dose disc when the upper proximal reservoir housing is rotated.

2. The inhaler according to claim 1, wherein the floor disc is connected to a lower distal twister.

3. The inhaler according to claim 2, wherein the floor disc is suspended above the lower distal twister.

4. The inhaler according to claim 1, wherein at least one of the chimney and the conduit includes deflectors.

5. The inhaler according to claim 1, further comprising a second medicament reservoir, wherein the dose disc has two cavities, each cavity configured to withdraw a dose of the medicaments from each of the first and second medicament reservoirs in the dose collecting position.

6. The inhaler according to claim 1, further comprising a second medicament reservoir, wherein the dose disc has four cavities and is configured such that a first set of two cavities lies underneath the air channels while a second set of two cavities is positioned in the medicament reservoirs.

7. The inhaler according to claim 1, wherein the cavity is circular and corresponds with a size of the overlying air channel.

8. The inhaler according to claim 1, wherein more than one cavity lies underneath the air channel, each cavity being of smaller size relative to the air channel.

9. The inhaler according to claim 1, wherein at least one medicament scraper is suspended in the at least one medicament reservoir, such that the at least one medicament scraper bears upon the dose disc.

10. The inhaler according to claim 9, wherein a number of scrapers in the medicament reservoir is selected in an interval from 1 to 6.

11. A dry powder inhaler comprising:
at least two air inlets, at least one air outlet, and at least two air channels each between a corresponding one of said at least two air inlets and said at least one air outlet;
at least one medicament reservoir;
a dosage mechanism for arranging at least one dose of a medicament from said at least one medicament reservoir between the air channel and the air outlet such that said at least one dose may be delivered upon inhalation at said air outlet, wherein the dosage mechanism comprises a dose disc with at least one cavity, and wherein the dose disc is rotatable between a dose collecting position, in which the cavity is positioned in the medicament reservoir, and a dose administering position, in which the cavity lies underneath one of the air channels, and wherein the dosage mechanism includes a mixing and deaggregation chamber between the at least two air channels, and a conduit extending distally from the mixing and deaggregation chamber towards the at least one air outlet;

a floor disc abutting the dose disc underneath the cavity to form a bottom of the cavity and support the medicament in the cavity, wherein said dose disc rotates in relation to the floor disc when the dose disc is rotated between the dose collecting position and the dose administering position to grind any residual medicament in the cavity; and an upper proximal reservoir housing with an inhalation chimney interconnecting the conduit and the air outlet, the inhalation chimney cooperating with the conduit to rotate the dose disc when the upper proximal reservoir housing is rotated.

12. The inhaler according to claim 11, wherein the floor disc is connected to a lower distal twister.

13. The inhaler according to claim 12, wherein the floor disc is suspended above the lower distal twister.

14. The inhaler according to claim 11, wherein the dose disc and the floor disc are rotated against each other by rotating the upper proximal reservoir housing and the lower distal twister in opposite directions simultaneously.

15. The inhaler according to claim 11, wherein at least one of the chimney and the conduit includes deflectors.

16. The inhaler according to claim 11, further comprising a second medicament reservoir, wherein the dose disc has two cavities, each cavity configured to withdraw a dose of the medicaments from each of the first and second medicament reservoirs in the dose collecting position.

17. The inhaler according to claim 11, further comprising a second medicament reservoir, wherein the dose disc has four cavities and is configured such that a first set of two cavities lies underneath the air channels while a second set of two cavities is positioned in the medicament reservoirs.

18. The inhaler according to claim 11, wherein the cavity is circular and corresponds with a size of the overlying air channel.

19. The inhaler according to claim 11, wherein more than one cavity lies underneath the air channel, each cavity being of smaller size relative to the air channel.

20. The inhaler according to claim 11, wherein at least one medicament scraper is suspended in the at least one medicament reservoir, such that the at least one medicament scraper bears upon the dose disc.

21. The inhaler according to claim 20, wherein a number of scrapers in the medicament reservoir is selected in an interval from 1 to 6.

* * * * *